United States Patent [19]

Goto et al.

[11] Patent Number: 5,059,627
[45] Date of Patent: Oct. 22, 1991

[54] NERVE GROWTH FACTOR SECRETION INDUCING COMPOSITION

[75] Inventors: Giichi Goto, Toyono; Kyozo Hayashi, Gifu, both of Japan

[73] Assignee: Takeda Chemical Industries, Ltd., Osaka, Japan

[21] Appl. No.: 487,249

[22] Filed: Mar. 2, 1990

[30] Foreign Application Priority Data

Aug. 24, 1989 [JP] Japan .................................. 218255

[51] Int. Cl.⁵ ...................... A01N 35/00; A01N 31/14
[52] U.S. Cl. ................................ 514/688; 514/718; 514/678; 514/685
[58] Field of Search ................ 514/718, 678, 685, 688

[56] References Cited

U.S. PATENT DOCUMENTS

| | | | |
|---|---|---|---|
| 4,393,075 | 7/1983 | Terao et al. | 424/304 |
| 4,436,753 | 3/1984 | Imada et al. | 424/331 |
| 4,851,413 | 7/1989 | Terao et al. | 514/277 |
| 4,851,414 | 7/1989 | Shizuo et al. | 514/277 |
| 4,851,431 | 7/1989 | Terao et al. | 514/277 |

FOREIGN PATENT DOCUMENTS 0171251 2/1986 European Pat. Off. .

OTHER PUBLICATIONS

Archives of Gerontology and Geriatrics, vol. 8, No. 3, 1989, pp. 191–373.

*Primary Examiner*— Friedman
*Assistant Examiner*—T. J. Criares
*Attorney, Agent, or Firm*—Wenderoth, Lind & Ponack

[57] ABSTRACT

A compound of the formula:

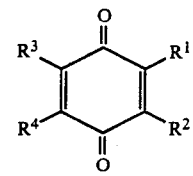

(I)

or

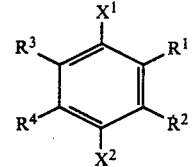

(II)

wherein $R^1$ is a lower alkyl group; $R^2$ is a hydrogen atom or an alkyl or alkenyl group which may be substituted; $R^3$ and $R^4$ each independently means a lower alkyl or lower alkoxy group or, taken together, mean a butadienylene group; and $X^1$ and $X^2$ each means a free hydroxy group or an esterified or etherified hydroxy group, has nerve growth factor secretion inducing activity, and a mammal suffering from degenerative nervous system disorders such as senile dementia, Alzheimer's disease, etc. is treated by administering said compound to said mammal.

4 Claims, 4 Drawing Sheets

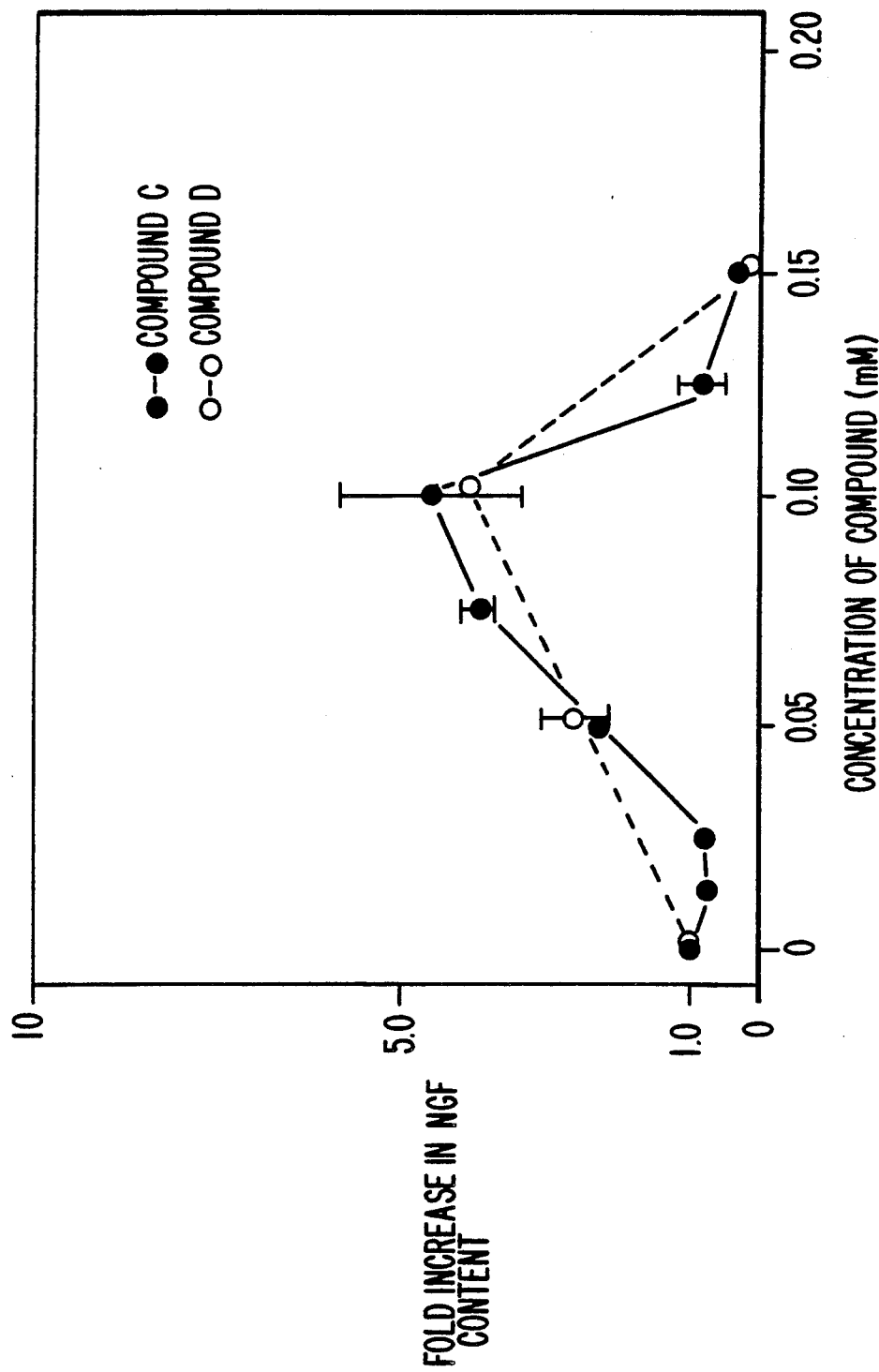

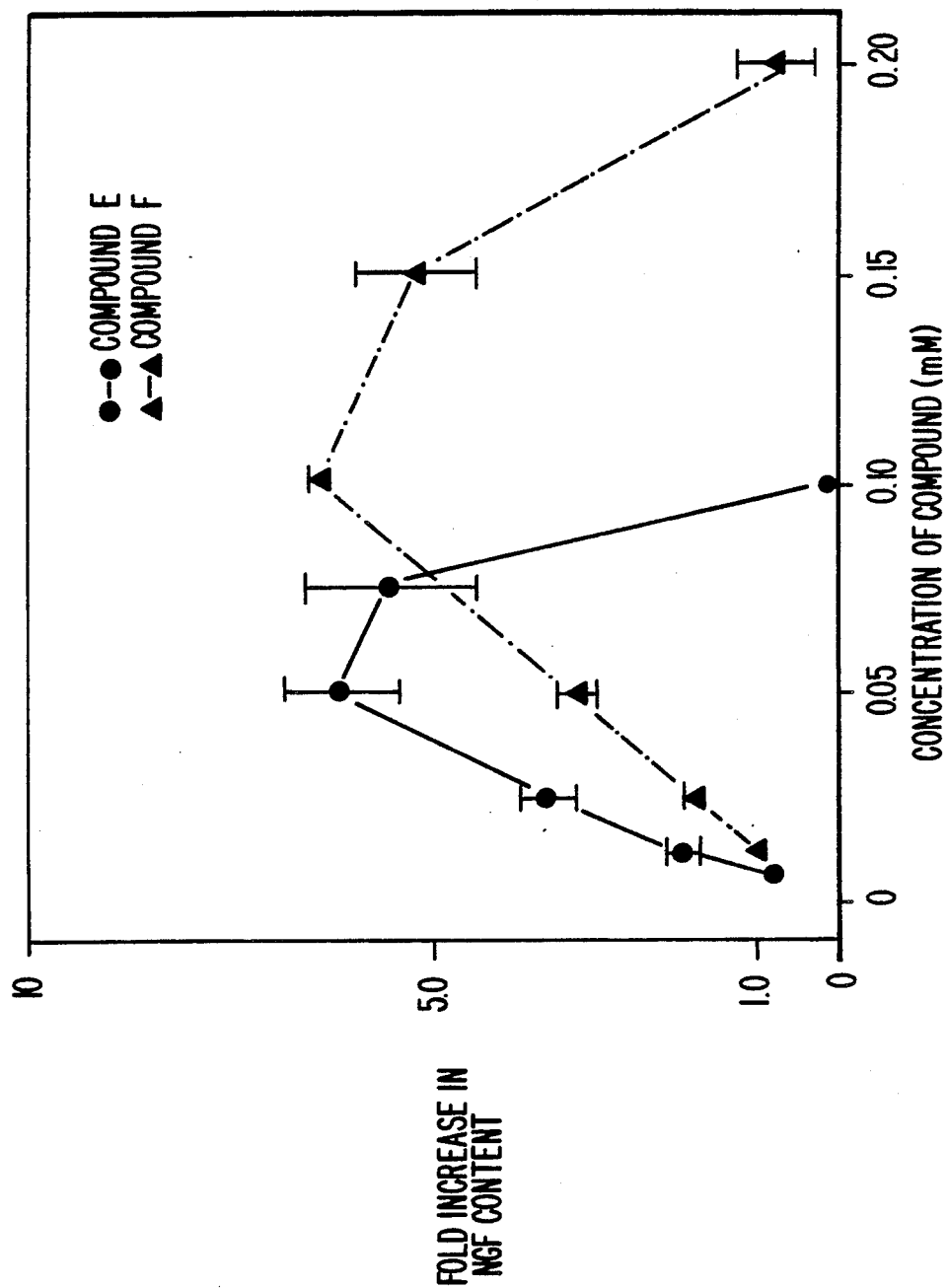

NERVE GROWTH FACTOR SECRETION INDUCING COMPOSITION

The present invention relates to a nerve growth factor secretion inducing composition which is of value as a medicine and particularly as a drug for the treatment or prevention of degenerative nervous system disorders associated with in senile dementia, Alzheimer's disease and so on.

With the on-going uptrend in age distribution of the population, a variety of brain function improving agents have been proposed.

Nerve growth factor (hereinafter referred to briefly as NGF) has been considered to be a nutrient factor essential to the maintenance of the living body, which serves to promote differentiation of the sympathetic and sensory nerve cells and brain nerve cells in the stage of genesis. The properties of NGF as a chemical substance (protein) have also been elucidated [Nature 302, 538, (1983)].

In patients with senile dementia or Alzheimer's disease, the biosynthesis and secretion of NGF are either at low levels or defected. Therefore, attempts have been made to use NGF in degenerative nervous system diseases such as senile dementia and Alzheimer's disease for the treatment of these maladies [Nature 329, 65, (1989)]. However, since the levels of biosynthesis and secretion of NGF are generally low, it is very difficult to isolate NGF from the living tissue or produce it by cloning in amounts useful for therapeutic and other purposes. On the other hand, it is known that NGF is synthesized de novo in the sympathetic and sensory nerve cells and brain nerve cells [Biochemical Biophysical Research Communications 136, 57, (1986)]. Under the circumstances, attempts have been made to stimulate the secretion of NGF in various nerve cells and cerebral neurons by means of catechol compounds [The Phramaceuticals Monthly 29, 49, (1987)]. However, these compounds are not satisfactory in the degree of activity or in the aspect of cytotoxicity.

From the above points of view, the inventors of the present invention did intensive research for developing an NGF secretion inducing agent that may take the place of cathecol compounds and have found that substituted 1,4-benzoquinone and substituted 1,4-hydroquinone derivatives have potent NGF secretion inducing activity with exceptionally low toxicity and high safety.

The present invention relates to a nerve growth factor secretion inducing composition, which comprises an effective amount of a compound of the general formula

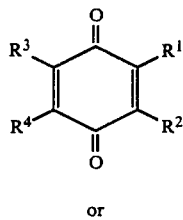

(I)

or (II)

wherein $R^1$ is a lower alkyl group; $R^2$ is a hydrogen atom or an alkyl or alkenyl group which may be substituted; $R^3$ and $R^4$ each independently means a lower alkyl or lower alkoxy group or, taken together, mean a butadienylene group; and $X^1$ and $X^2$ each means a free hydroxy group or an esterified or etherified hydroxy group, in admixture with a pharmaceutically acceptable carrier therefor.

The present invention also relates to a method for the prophylaxis or treatment of degenerative nervous system disorders which comprises administering to a mammal suffering from said disorders an effective amount of a compound of the formula (I) or (II).

Referring to the above general formulas (I) and (II), the lower alkyl group $R^1$ is a lower alkyl group of 1 to 4 carbon atoms, such as methyl, ethyl, propyl, butyl and so on. The alkyl moiety of the unsubstituted or substituted alkyl group $R^2$ includes acyclic hydrocarbon residues of 1 to 22 carbon atoms, such as methyl, ethyl, propyl, butyl, pentyl, hexyl, heptyl, octyl, nonyl, decyl, undecyl, dodecyl, tridecyl, pentadecyl, heptadecyl, eicosyl, docosyl and so on. Among them, an alkyl having 8 to 13 carbon atoms is preferable.

The alkenyl moiety of the unsubstituted or substituted alkenyl group $R^2$ include acyclic hydrocarbon residues of 2 to 15 carbon atoms, such as ethenyl, 1-propenyl, 3-methyl-2-butenyl, 3,7-dimethyl-2,6-octadienyl, etc., wherein the number of double bonds may generally range from 1 to 3 and these double bonds may be conjugated. Examples of substituents on the alkyl and alkenyl groups $R^2$ include hydroxy, carboxy, alkoxycarbonyl (e.g. $C_{1-4}$ alkoxycarbonyl groups such as methoxycarbonyl, ethoxycarbonyl, propionyloxycarbonyl, butoxycarbonyl, etc.), aryl (e.g. phenyl, 1-naphthyl, 2-naphthyl, indanyl, etc.), heterocyclic groups (e.g. 2-pyridyl, 3-pyridyl, 2-thienyl, 3-thienyl, etc.) and halogen (e.g. fluorine, chlorine, bromine and iodine). Where the substituent group is such an aryl group or a heterocyclic group, the group may be nuclearly substituted by one or more substituents in optional positions of the ring structure. The substituents mentioned just above include, but are not limited to, unsubstituted $C_{1-4}$ alkyl groups (e.g. methyl, ethyl, propyl, butyl, etc.), hydroxy, carboxy, and $C_{2-5}$ alkoxycarbonyl (e.g. methoxycarbonyl, ethoxycarbonyl, propoxycarbonyl, butoxycarbonyl, etc.). The position of substitution on the alkyl or alkenyl group $R^2$ is optional but preferably 1-position or ω-position. The lower alkyl group, represented by $R^3$ and $R^4$, may be a $C_{1-6}$ alkyl group, such as methyl, ethyl, propyl, i-propyl, butyl, i-butyl, sec-butyl, t-butyl, amyl, hexyl, etc. and preferably a $C_{1-3}$ alkyl group. These lower alkyl groups may have substituents such as hydroxy, halogen (fluorine, chlorine, bromine and iodine), nitro, trifluoromethyl, carboxy, $C_{2-5}$ alkoxycarbonyl (e.g. methoxycarbonyl, ethoxycarbonyl, etc.), 3-pyridyl, 1-imidazolyl, 5-thiazolyl and so on. The lower alkoxy group, represented by $R^3$ and $R^4$, may be a $C_{1-3}$ alkoxy group such as methoxy, ethoxy, propoxy, i-propoxy and so on. Where $R^3$ and $R^4$ mean a butadienylene group, they constitute a benzene ring in association with the carbon atoms to which $R^3$ and $R^4$ are respectively attached, and the benzene ring so constituted may have 1 to 3 substituent groups in optional positions, which substituent groups include, among others, lower ($C_{1-3}$) alkyl groups (e.g. methyl, ethyl, propyl, etc.), lower ($C_{1-3}$) alkoxy groups (e.g. methoxy, ethoxy, propoxy, etc.), hydroxy, nitro and halogen.

Referring to the above general formula (II), the etherified hydroxy group mentioned for $X^1$ and $X^2$ includes alkoxy and aralkyloxy groups, among others. The alkoxy groups mentioned just above may be $C_{1-8}$ alkoxy groups such as methoxymethoxy, ethoxy, propoxy, i-propoxy, butoxy, i-butoxy, t-butoxy, sec-butoxy, amyloxy, hexyloxy, tetrahydropyranyloxy, tetrahydrofuryloxy, etc., and $C_{1-3}$ alkoxy groups are particularly preferred. The aralkyloxy groups, also mentioned above, may be $C_{7-8}$ aralkyloxy groups such as benzyloxy. The esterified hydroxy groups include carboxylic acid-derived acyloxy groups and phosphoric acid-derived acyloxy groups. The acyl moiety of such a carboxylic acid-derived acyloxy group includes, among others, acyclic or cyclic $C_{3-10}$ alkanoyl groups such as formyl, acetyl, propionyl, isobutyryl, decanoyl, cyclopentyl, cyclohexylcarbonyl, etc., arylcarbonyl groups such as benzoyl etc., and nicotinoyl which may optionally be quaternized, succinic acid hemiacyl and so on.

The compounds (I) and (II) may form various salts according to the kinds of substituents thereon, such as salts with organic acids (e.g. acetic acid, propionic acid, oxalic acid, maleic acid, etc.), salts with inorganic acids (e.g. hydrochloric acid, sulfuric acid, phosphoric acid, etc.), salts with alkali metals (e.g. potassium, sodium, etc.), alkaline earth metals (e.g. calcium, magnesium, etc.), and ammonium salts. Particularly preferred are physiologically acceptable salts.

The compounds (I) and (II) can be produced by the per se known processes, for example as described in Chemical and Pharmaceutical Bulletin 30, 2797, 1982 and 33, 4422, 1985 and Japanese Patent Application KOKAI 51-128932, KOKAI 63-045257, KOKAI 57-109739 and KOKAI 61-044840.

Among the compounds of general formulas (I) and (II), highly centrally-oriented species, such as 6-(10-hydroxydecyl)-2,3-dimethoxy-5-methyl-1,4-benzoquinone, 6-(10-hydroxydecyl)-2,3-dimethoxy-5-methyl-1,4-hydroquinone, and 2,3,5-trimethyl-1,4-benzoquinone are preferred for the purposes of the invention.

For application as a nerve growth factor secretion inducing agent, the compounds of the formulas (I) and (II) can be formulated into various dosage forms, such as tablets, granules, capsules, injections, suppositories, etc., in the per se conventional manner and the resulting preparations can be administered, orally or otherwise, to mammals including man. The dosage should be optimized according to the disease to be treated, the condition of the patient and other factors but generally the usual oral dosage for adult humans is 0.1 mg to 500 mg/day and preferably 5 to 200 mg/day.

The nerve growth factor secretion inducing composition of the invention is useful for the treatment and prevention of functional disorders of the brain in mammarian animals including man, and the anticipated indications include familial dysautonomia, neurofibroma, neuroblastoma, melanocytoma, senile dementia, Alzheimer's disease and so on.

The following test and preparation examples are intended to illustrate the effect and manner of application of the invention in detail.

TEST EXAMPLE 1 i) Experimental materials and method

The study of NGF biosynthesis using astroglial cells is a very interesting line of research in connection with senile dementia of the Alzheimer's disease type. Therefore, the NGF biosynthesis promoting activity of the compound of the invention was studied using mouse astroglial cells (MB-8 cells). In the study, MB-8 cells in the stationary phase which was considered to be closer to the condition in the normal brain than the cells in the growth phase were used.

a) Experimental materials

The astroglial (MB-8) cells were a generous gift from National Center of Neurology and Psychiatry (Dr. Shoei Furukawa). DMEM (Dulbecco's modified Eagle medium) was purchased from Nissui Pharmaceutical Co., Ltd, fetal calf serum (FCS) from Bocknek, and streptomycin sulfate and benzylpenicillin potassium from Meiji Seika Kaisha, Ltd. The 24-well microtiter plate manufactured by Falcon was used. All the other reagents were of commercial special reagent grade.

b) Method

Culture of MB-8 cells

The astroglial (MB-8) cells from the brain of 8-day-old mice were cultured in DMEM containing 10% FCS, glutamin (2 mM), penicillin (100 units/ml) and streptomycin (100 μg/ml) in a carbon dioxide gas incubator (37° C., 5% $CO_2$). The procedure was repeated a few times until confluent growth was obtained. Then, the cells were further cultured in DMEM containing 5% BSA in lieu of FCS for about 10 days to bring the cells into a stationary phase of growth. The resulting cells were grown in DMEM containing 0.5% BSA to which various compounds had been added for 24 hours. The supernatant was collected and the NGF content was determined by the under-mentioned enzyme immunoassay method using mouse β NGF.

ii) Enzyme immunoassay (EIA) of NGF

Anti-mouse β-NGF antibody immunoglobulin G (IgG) (10 μg/ml) prepared using Protein A-Sepharose CL-4B and diluted with 0.05M Tris-HCl buffer (pH 8.3) was distributed in 10 μM portions into the wells of a polystyrene microtiter plate (Falcon 3910; 96-well) and allowed to stand at room temperature for 2 hours to adsorb the anti-mouse βNGF antibody IgG. After recovery of the antibody solution, the plate was washed three times with 100 μM portions of a washing buffer (0.1M Tris-HCl buffer containing 0.4M sodium chloride, 0.1% BSA, 0.1% sodium azide and 1 mM magnesium chloride; pH 7.6). Then, 150 μM of the washing buffer was added for 1 hr of blocking. After the washing buffer was aspirated off, 25 μM portions of the sample or the standard NGF solution (as diluted with the same buffer as for the sample) were added to the wells and allowed to stand at room temperature for 4 hours. The plate was then washed with three 100 μM portions of the washing buffer and 30 ml portions of a biotinylated anti-βNGF antibody solution diluted with the washing buffer (35 ng/ml) were added. The plate was allowed to stand at 4° C. overnight. After washing, 30 ml of β-D-galactosidase-labeled streptavidin (diluted 200-fold) was added and the plate was allowed to stand at room temperature for 1 hour. The activity of the β-D-galactosidase immobilized on the solid phase was estimated by measuring the fluorescence of the 4-methylumbelliferone produced by reaction with the substrate 4-methylumbelliferyl-β-galactoside. Thus, after the plate was washed 3 times, 30 μM portions of the substrate (10 μg/ml) were added and the reaction was conducted at room temperature for 3 hours. The enzymatic reaction was stopped by adding 150 μM of 0.1 M glycine-sodium hydroxide buffer (pH 10.3) and the reaction systems were transferred to test tubes each containing 2.0 ml of the reaction stopper. The intensity of fluorescence in each tube was measured at an excitation wavelength of 360 nm and an emission wavelength of 450 nm. The fluorophotometer was calibrated by adjusting the fluorescence intensity of 0.1N sulfuric acid containing 1 μg/ml of quinine to 100.

iii) Results a) The standard curve of mouse βNGF

The EIA standard curve for mouse βNGF according to the method mentioned above is shown in FIG. 1. While determinations were performed over the range of 0.15 pg/ml to 9 ng/ml, the curve flattened into a plateau after 9 ng/ml. The measuring range was 1 pg/ml to 9 ng/ml.

The background was low and the differential in the intensity of fluorescence between 1 pg/ml and 9 ng/ml was about 100-fold so that the concentration of NGF was easy to read. The sensitivity of this assay method was as high as about 1 pg/ml.

b) The effect of the compound of the invention on the synthesis and secretion of NGF in MB-8 cells.

FIG. 3 shows the NGF secretion inducing effects of 2,3-dimethoxy-5-methyl-1,4-benzoquinone (Compound C) and ubiquinone-2 (Compound D).

FIG. 4 shows the NGF secretion inducing effects of vitamin $K_0$ (Compound E) and 2,3,5-trimethyl-1,4-hydroquinone (Compound F).

TEST EXAMPLE 2

Figure 1:
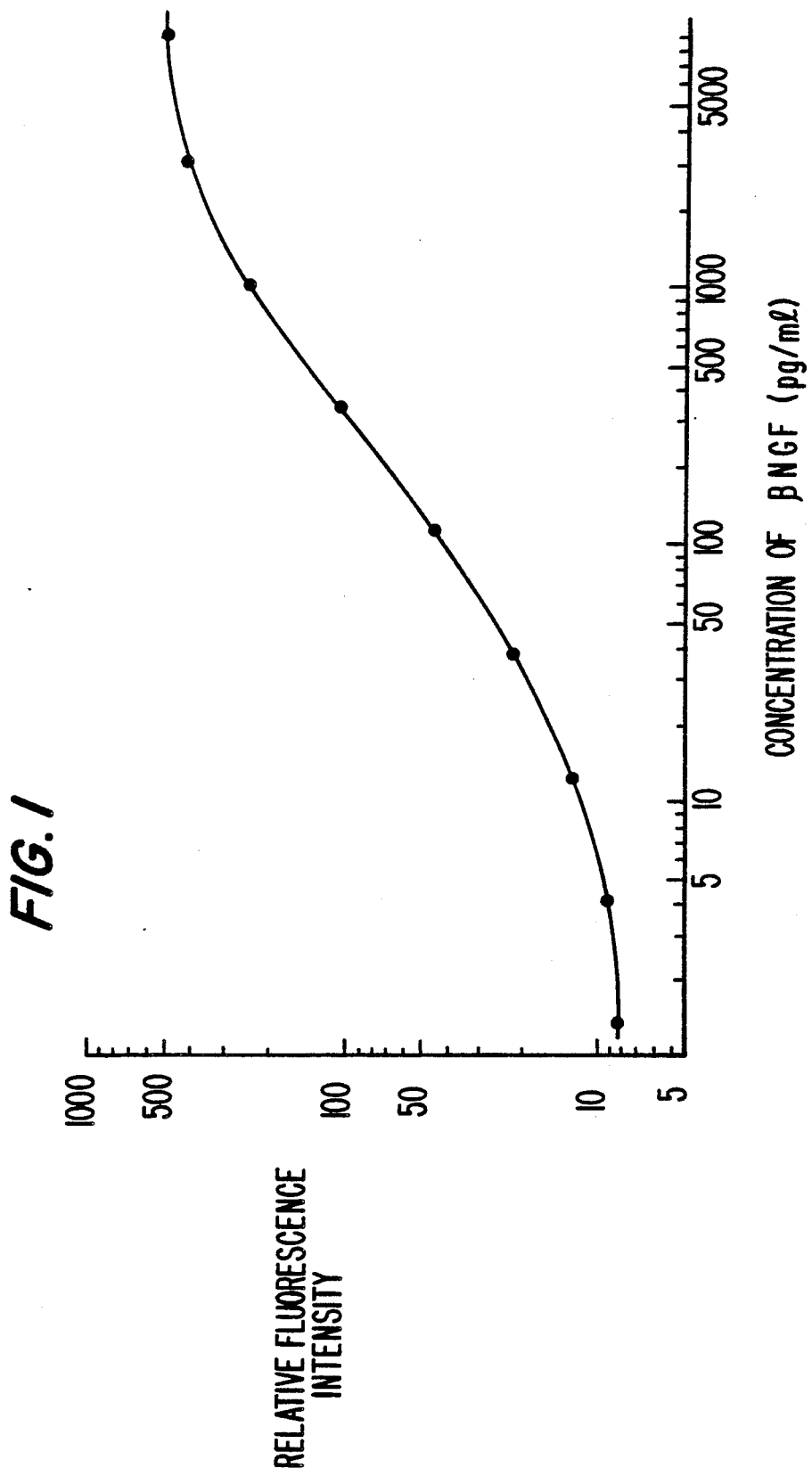
Figure 2:
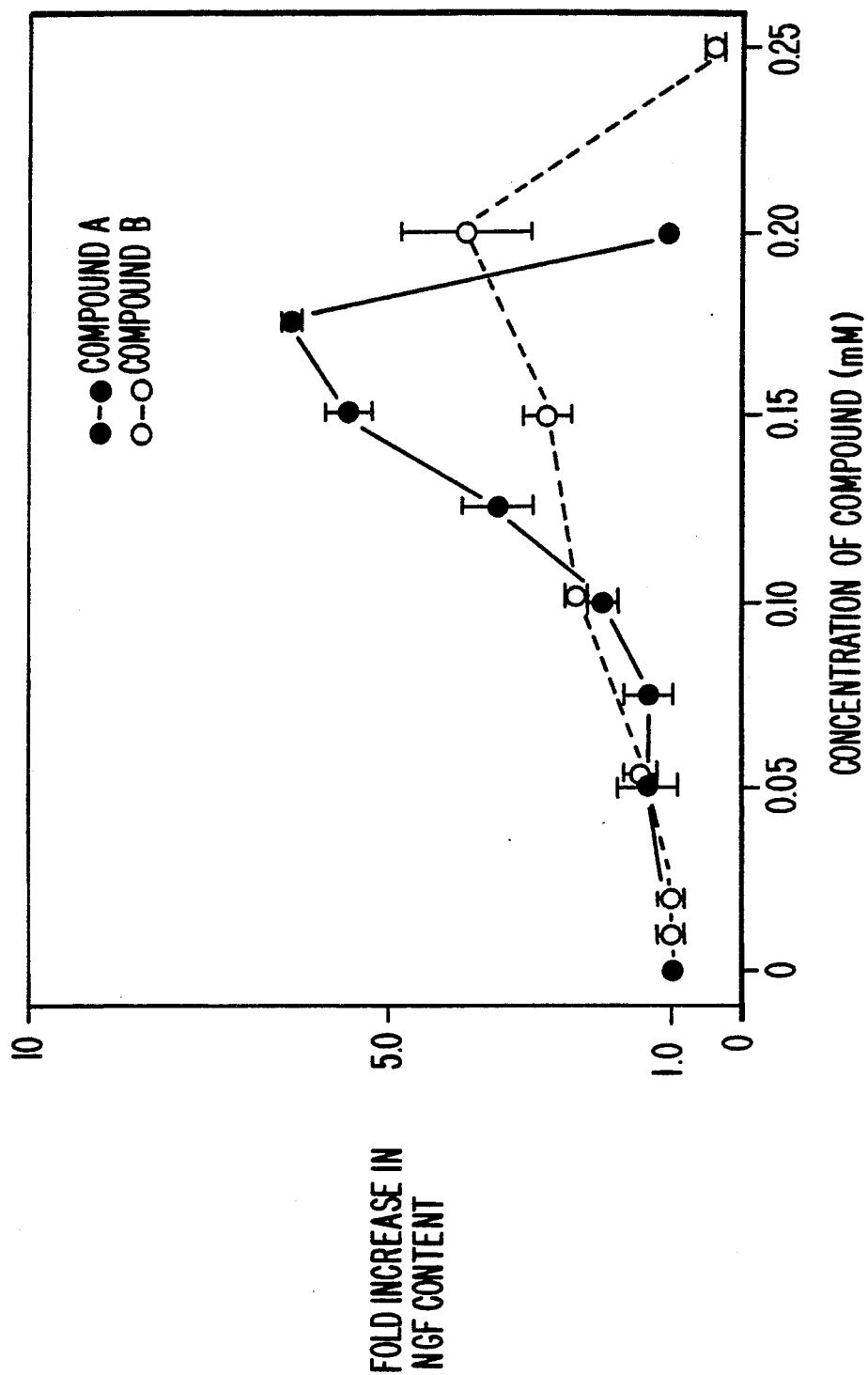
FIG. 2 shows the NGF secretion inducing effects of 6-(10-hydroxydecyl)-2,3-dimethoxy-5-methyl-1,4-benzoquinone (Compound A) and 6-(10-hydroxydecyl)-2,3-dimethoxy-5-methyl-1,4-hydroquinone (Compound B).

(the acute toxicity of compounds of the invention)

$LD_{50}$ in mice

Using mice in groups of 10, the dose (mg/kg, p.o) ($LD_{50}$) killing one-half of the animals was determined. The results are set forth in Table 1.

TABLE 1

| Compound | $LD_{50}$ (mg/kg, po) |
| --- | --- |
| 6-(10-Hydroxydecyl)-2,3-dimethoxy-5-methyl-1,4-benzoquinone | >1000 |
| 6-(10-Hydroxydecyl)-2,3-dimethoxy-5-methyl-1,4-hydroquinone | >1000 |
| 2,3-Dimethoxy-5-methyl-1,4-benzoquinone | >500 |
| Ubiquinone-2 | >500 |
| Vitamin $K_0$ | 500 |
| 2,3,5-Trimethyl-1,4-hydroquinone | >500 |

PREPARATION EXAMPLE 1

| (1) | 6-(10-Hydroxydecyl)-2,3-dimethoxy-5-methyl-1,4-hydroquinone | 20 g |
| --- | --- | --- |
| (2) | Lactose | 198 g |
| (3) | Corn starch | 40 g |
| (4) | Magnesium stearate | 2 g |

The above ingredients (1) and (2) and a paste prepared from a 15 g portion of corn starch (3) were mixed and granulated, followed by adding a 10 g portion of corn starch and (4). The resulting mixture was compression-molded to prepare 1000 tables measuring 5 mm in diameter and each containing 20 mg of (1).

We claim:

1. A method for inducing nerve growth factor secretion for the prophylaxis or treatment of degenerative nervous system disorders which comprises administering to a mammal suffering from said disorders an effective amount of a compound of the formula:

[structure with $R^1$, $R^2$, $R^3$, $R^4$ on a 1,4-benzoquinone]

or

[structure with $R^1$, $R^2$, $R^3$, $R^4$, $X^1$, $X^2$ on a benzene ring]

wherein $R^1$ is a lower alkyl group; $R^2$ is a hydrogen atom or an alkyl or alkenyl group which may be substituted; $R^3$ and $R^4$ each independently means a lower alkyl or lower alkoxy group or, taken together, mean a butadienylene group; and $X^1$ and $X^2$ each means a free hydroxy group, $C_{1-8}$ alkoxy, $C_{7-8}$ aralkoxy, acyclic or cyclic $C_{8-10}$ alkanoyloxy or phosphoric acid-derived acyloxy.

2. A method as claimed in claim 1, wherein $R^2$ is hydrogen, a hydroxyalkyl having 8 to 13 carbon atoms or a group of the formula:

$$\left( \phantom{x} \begin{array}{c} \\ CH_3 \end{array} \right)_n H$$

wherein n is 2 or 3.

3. A method as claimed in claim 1, wherein $R^2$ is hydrogen, 10-hydroxydecyl, 3,7-dimethyl-2,6-octadienyl or 3,7,11-trimethyl-2,6,10-dodecatrienyl.

4. A method as claimed in claim 1, wherein degenerative nervous system disorder is Alzheimer's disease.

* * * * *